United States Patent
Swartz et al.

(10) Patent No.: US 7,351,563 B2
(45) Date of Patent: Apr. 1, 2008

(54) CELL-FREE EXTRACTS AND SYNTHESIS OF ACTIVE HYDROGENASE

(75) Inventors: James Robert Swartz, Stanford, CA (US); Marcus Emil Boyer, Palo Alto, CA (US); James Alan Stapleton, Los Altos, CA (US); Alfred M. Spormann, Stanford, CA (US); Chia-Wei Wang, Cupertino, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 314 days.

(21) Appl. No.: 11/149,517

(22) Filed: Jun. 10, 2005

(65) Prior Publication Data
US 2006/0281148 A1    Dec. 14, 2006

(51) Int. Cl.
*C12N 9/02* (2006.01)
(52) U.S. Cl. .................... 435/189; 435/68.1; 435/69.1; 536/23.2
(58) Field of Classification Search .............. 435/189, 435/68.1, 69.1; 536/23.2
See application file for complete search history.

(56) References Cited

U.S. PATENT DOCUMENTS 6,337,191 B1 * 1/2002 Swartz et al. .............. 435/68.1

2002/0081660 A1    6/2002 Swartz
2004/0209321 A1   10/2004 Swartz

FOREIGN PATENT DOCUMENTS

| WO | WO00/55353 | 9/2000 |
|---|---|---|
| WO | WO2004/016778 | 2/2004 |
| WO | WO2005/010155 | 2/2005 |
| WO | WO 2006/093998 A2 * | 9/2006 |

OTHER PUBLICATIONS

Posewitz et al., Discovery of two novel radical S-adenosylmethionine proteins required for the assembly of an active [Fe] hydrogenase, J Biol Chem. Jun. 11, 2004;279(24):25711-20. Epub 2004.

* cited by examiner

*Primary Examiner*—Tekchand Saidha
(74) *Attorney, Agent, or Firm*—Bozicevic, Field & Francis LLP; Pamela J. Sherwood

(57) ABSTRACT

Enzymatically active hydrogenase is synthesized in a cell-free reaction. The hydrogenases are synthesized in a cell-free reaction comprising a cell extract derived from microbial strains expressing at least one hydrogenase accessory protein. In some embodiments, the extracts are produced under anaerobic conditions.

11 Claims, 6 Drawing Sheets

CELL-FREE EXTRACTS AND SYNTHESIS OF ACTIVE HYDROGENASE

Current traditional energy technologies rely on fossil fuels. Their most significant limitations are the depletion of limited fossil fuel reservoirs, thus, making this a non-sustainable technology, and the net generation of $CO_2$ and other greenhouse gases, thereby affecting the global climate in a fundamental and uncontrollable manner. Hydrogen gas is a renewable energy source that does not evolve the "greenhouse gas" $CO_2$ in combustion, liberates large amounts of energy per unit weight in combustion, and is easily converted to electricity by fuel cells.

However, current sources of hydrogen often rely on fossil fuels as input material. The use of hydrogen as a large scale fuel therefore depends, in part, on developing new hydrogen sources. One path of particular interest is biological hydrogen production from sunlight, enabled by genetically engineered photosynthetic microbes that express hydrogenases—enzymes that catalyze the reversible reduction of protons into $H_2$.

Biological hydrogen production has several advantages over hydrogen production by photoelectrochemical or thermochemical processes. Biological hydrogen production by photosynthetic microorganisms, for example, requires the use of a simple solar reactor such as a transparent closed box, with low energy requirements. An ideal process to produce $H_2$ more economically would be to use water as an input, and photosynthetic processes to generate the energy needed for reduction.

The naturally occurring photosystems are unable to meet this need. Lacking photosystem II, photosynthetic bacteria cannot use water as the electron donor, although Cyanobacteria such *Synechocystis* have both photosystems I and II and can oxidize water to generate photoreductants. However, most $H_2$-evolving hydrogenases are extremely sensitive to $O_2$, which is an inherent byproduct of cyanobacterial photosynthesis. Therefore, to establish a successful cyanobacterium-bacterium hybrid system using $H_2O$ as the electron donor, one critical requirement is to use a hydrogenase that is not only tolerant to $O_2$ but also catalytically active in $O_2$.

Oxygen tolerant hydrogenases have not been found in nature, and so there is considerable interest in the genetic engineering of such a protein. Various approaches can be utilized for the modification, however an efficient means of producing the protein, high throughput screening for activity, as well as means of generating sequence variants, must be available. The present invention addresses these problems.

Literature citations. Posewitz et al. (2004) J Biol Chem. 279(24):25711-20 describe radical S-adenosylmethionine proteins required for the assembly of an active [Fe] hydrogenase. Methods of cell-free protein synthesis are described, for example, in U.S. Pat. No. 6,337,191 B1; U.S. Patent Published Application 20020081660; U.S. Patent Published Application 20040209321; and International Applications WO2004/016778; WO 2005/010155; WO 00/55353; and WO 00/55353, each herein incorporated by reference.

SUMMARY OF THE INVENTION

Compositions and methods are provided for the cell-free synthesis of enzymatically active hydrogenase. Hydrogenases of interest include iron hydrogenases that primarily catalyze $H_2$ evolution, e.g. *Chlamydomonas reinhardtii* iron-hydrogenase; *Clostridium pasteurianum* hydrogenase; *Megasphaera elsdenii* hydrogenase; derivatives; variants; homologs; and the like. The hydrogenases are synthesized in a cell-free reaction comprising a cell extract derived from microbial strains expressing at least one hydrogenase accessory protein. In some embodiments, the extracts are produced under anaerobic conditions.

DETAILED DESCRIPTION OF THE EMBODIMENTS

Figure 1:
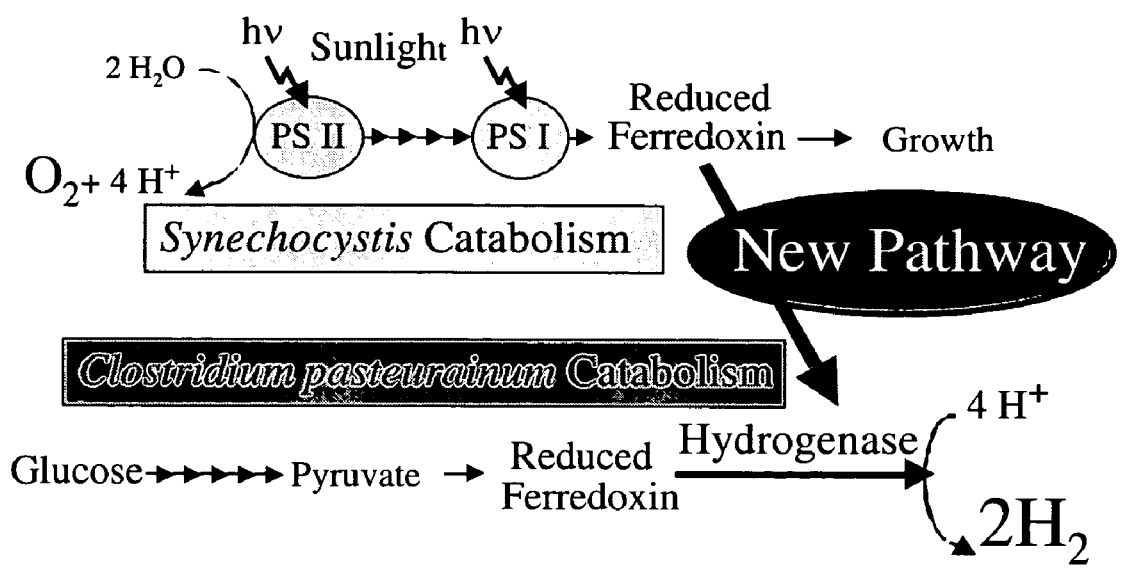
FIG. 1 is a schematic illustrating energy flow in a system for photosynthetic $H_2$ production.

Methods are provided to synthesize enzymatically active hydrogenase in a cell-free reaction mix. Hydrogenases of interest catalyze $H_2$ evolution, and include without limitation the monomeric iron hydrogenases, e.g. *Chlamydomonas reinhardtii* iron-hydrogenase; *Clostridium pasteurianum* hydrogenase; *Megasphaera elsdenii* hydrogenase; including variants and derivative thereof, and the like. Because of the complexity of the protein assembly and folding, it was unexpected that a cell extract derived from microbial strains expressing at least one hydrogenase accessory protein could provide for in vitro synthesis of active hydrogenase.

In one embodiment of the invention, a cellular extract of a bacterial strain is provided in which genetic sequences encoding at least one hydrogenase accessory protein is expressed. The use of *E. coli* is of particular interest, where the accessory proteins are exogenous to the host cell, and may include one, two or all of a HydE; HydF; and/or HydG polypeptide obtained from any suitable hydrogenase producing host, e.g. *Shewanella, Chladymonas, Clostridia*, etc. Additional genetic modifications may also be made to the microbial strain, for example the deletion of tonA and endA genes to protect against bacteriophage infection and stabilize DNA within the system, the deletion of proteins involved in amino acid degradation, and the like.

The extract may be provided in a fresh or frozen form, and may further be formulated into a reaction mix suitable for polypeptide synthesis. Such extracts are obtained by any of the methods known in the art for the purpose of cell-free protein synthesis, with the modification that the extract may be prepared under anaerobic conditions for the final stages of preparation. In one example of such methods, cells are grown in defined media under aerobic conditions to the appropriate optical density for induction of hydrogenase accessory protein synthesis. After induction of accessory protein expression, the culture is switched to anaerobic conditions, for example by bubbling nitrogen, argon, etc. through the culture medium. The cells are harvested by centrifugation and washed in S30 buffer. Preferably, care is taken during the harvest procedure to maintain anaerobiosis.

After the final wash, the cells are resuspended in S30 buffer and disrupted, e.g. with a French press. The lysate is then centrifuged, and the withdrawn supernatant used as the extract. The extract is prepared in an anaerobic chamber, and any contaminating oxygen is actively scrubbed from the chamber atmosphere, for example, by reaction with hydrogen on palladium catalysts. One dialysis step of 45 minutes is employed before the extract is aliquotted, sealed in anaerobic vials, and flash frozen using liquid nitrogen. The extract may be stored at −80° C. until needed for cell-free protein synthesis.

In another embodiment of the invention, methods of cell-free polypeptide synthesis are provided, where the reaction mixture comprises a cell extract as described above. Surprisingly, it is shown herein that an extract for cell-free synthesis of active hydrogenase demonstrated to be capable of evolving $H_2$ in vitro can be produced. The cell-free system offers a flexible format for protein expression. This flexibility allows for numerous modifications to the compositions of the system without adversely affecting the advantages gained by this new technology.

Hydrogenase. Hydrogenases catalyse the reversible oxidation/reduction of molecular hydrogen ($H_2$) and play a vital role in anaerobic metabolism. Metal containing hydrogenases are subdivided into three classes: Fe hydrogenases, Ni—Fe hydrogenases, and Ni—Fe—Se hydrogenases. Hydrogen oxidation is coupled to the reduction of electron acceptors such as oxygen, nitrate, sulphate, carbon dioxide and fumarate, whereas proton reduction ($H_2$ evolution) is coupled to molecules such as ferredoxin. The methods of the invention may be applied to any of the hydrogenases.

In one embodiment, the term "hydrogenase" as used herein refers to an enzyme that meets one or more of the criteria provided herein. Using these criteria, one of skill in the art can determine the suitability of a candidate enzyme for use in the methods of the invention. Many enzymes will meet multiple criteria, including two, three, four or more of the criteria, and some enzymes will meet all of the criteria. The terms "hydrogenase" can refer to a full length enzyme or fragment thereof with the capability of catalyzing hydrogen oxidation/reduction.

Hydrogenases of the invention include enzymes having at least about 20% sequence identity at the amino acid level, more usually at least about 40% sequence identity, and preferably at least about 70% sequence identity to one of the following hydrogenases: *Chlamydomonas reinhardtii* iron-hydrogenase (Genbank accession AY055756); *Clostridium pasteurianum* hydrogenase (Genbank accession AAA23248.1); *Megasphaera elsdenii* hydrogenase (Genbank accession AF120457); *Desulfovibrio vulgaris* hydrogenase (Genbank accession CA26266.1). For example, see Forestier et al. (2003) Eur. J. Biochem. 270 (13), 2750-2758; Meyer et al. (1991) Biochemistry 30:9697-9704; Voordouw et al. (1985) Eur. J. Biochem. 148:515-520; Atta et al. (2000) Biochim Biophys Acta. 1476(2):368-71; Fauque et al. (1988) FEMS Microbiol. Rev. 4, 299-344; Cammack et al. (1994) Methods Enzymol. 243, 43-68; and de Lacey et al. (1997) J. Am. Chem. Soc. 119, 7181-7189, each herein incorporated by reference.

Homology-based identification (for example, by a PILEUP sequence analysis) of enzymes can be routinely performed by those of skill in the art upon contemplation of this disclosure to identify those suitable for use in the methods of the present invention. Such enzymes are usually produced in microorganisms, particularly bacteria. Hydrogenases of the invention also include an enzyme belonging to the enzyme classifications EC 1.12.7.2 and EC 1.12.2.1.

The nucleic acid sequences encoding the above hydrogenases may be accessed from public databases as previously cited. Identification of additional hydrogenases is accomplished by conventional screening methods of DNA libraries or biological samples for DNA sequences having a high degree of similarity to known hydrogenase sequences.

The sequence of hydrogenases may be altered in various ways known in the art to generate targeted changes in sequence. The sequence changes may be substitutions, insertions or deletions. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

The peptides may be joined to a wide variety of other oligopeptides or proteins for a variety of purposes. By providing for expression of the subject peptides, various post-expression modifications may be achieved. For example, by employing the appropriate coding sequences, one may provide farnesylation or prenylation. The peptides may be PEGylated. The peptides may also be combined with other proteins to produce a fusion polypeptide.

Modifications of interest that do not alter primary sequence include chemical derivatization of polypeptides, e.g., acylation, acetylation, carboxylation, etc. Also embraced are sequences that have phosphorylated amino acid residues, e.g. phosphotyrosine, phosphoserine, or phosphothreonine.

Modifications may also be made to the hydrogenase coding sequence. In addition to changes in the polypeptide sequence, silent changes in the polynucleotide coding sequence are also of interest, in order to optimize for codon usage of the bacterial strain from which the extract is derived. For example, where the extract is derived from *E. coli*, the codon usage in the hydrogenase coding sequence may be optimized for *E. coli* translation. Methods for such optimization are known in the art, e.g. as set forth in Grosjean and Fiers (1982) Gene 18(3):199-209; Yadava and Ockenhouse (2003) Infection and Immunity 71(9):4961-4969; Gutierrez et al. Nucleic Acids Research 24(13):2525-2527; and Akashi and Gojobori (2002) PNAS 99(6): 3695-3700.

Also included in the subject invention are peptides that have been modified using ordinary molecular biological techniques and synthetic chemistry so as to improve their resistance to proteolytic degradation or to optimize solubility properties, etc. Analogs of such polypeptides include those containing residues other than naturally occurring L-amino acids, e.g. D-amino acids or non-naturally occurring synthetic amino acids. D-amino acids may be substituted for some or all of the amino acid residues. If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. The reaction mixture may be purified using HPLC, exclusion chromatography, gel electrophoresis, affinity chromatography, or other purification technique.

Iron hydrogenase. The hydrogenases containing no other metal than Fe are called Fe hydrogenases (Fe-Hases), also known as "Fe-only" hydrogenases. Two families of Fe-Hases have been described. Cytoplasmic, soluble, monomeric Fe-Hases are found in strict anaerobes such as *Clostridium pasteurianum* and *Megasphaera elsdenii*. They are extremely sensitive to inactivation by $O_2$ and catalyse both $H_2$ evolution and uptake. Periplasmic, heterodimeric Fe-Hases from *Desulfovibrio* spp., can be purified aerobically but catalyse mainly $H_2$ oxidation.

3-D structures of $H_2$ evolving Fe-Hase I from *Clostridium pasteurianum* (CpI) and *Desulfovibrio desulfuricans* uptake hydrogenase (DdH) are known. The overall structure of CpI resembles a mushroom consisting of four domains: the large active site domain forms "cap" and three smaller domains form "stem". The "stem" domains bind four iron-sulphur clusters and are termed FS4A-FS4B, FS4C and FS2. The N-terminal FS2 domain binds a $[Fe_2S_2]$ cluster and shares the overall fold with plant-type ferredoxins. The FS4A-FS4B domain is adjacent to the active site domain; it contains two $[Fe_4S_4]$ clusters and has the overall fold similar to that of bacterial type ferredoxins. The FS4C domain is placed between the FS2 and FS4A-FS4B domains and consists of two α-helices linked by a loop that binds a single $[Fe_4S_4]$ cluster via one His and three Cys residues. The large subunit of DdH lacks FS4C and FS2 clusters and corresponding domains. The small subunit of DdH has an unusual fold consisting of alternating random coil and four α-helices that form a "belt" around the large subunit.

The active site domain of the Fe-Hases contains an unusual Fe—S centre termed the H-cluster. H-cluster consists of the $[Fe_4S_4]$ subcduster bridged via the Cys thiolate to the $[Fe d_2]$ (binuclear iron) subcluster. The two iron atoms are designated Fe1 and Fe2 (proximal and distal with respect to the $[Fe_4S_4]$ subcluster) and are ~2.6 Å apart. With the exception of the bridging Cys, the diiron subcluster is coordinated by non-protein ligands. In CpI, both iron atoms are octahedrally coordinated to five CO/CN ligands, three S ligands and one water molecule. Fe1 and Fe2 are bridged by two S atoms and one CO or CN ligand. The two bridging sulphurs themselves are bridged by atom(s) of unknown identity. In DdH, Fe1 and Fe2 are bridged by a small molecule that has been modelled as 1,3-propanedithiol (PDT). Fe1 is octahedrally coordinated while Fe2 has square pyramidal coordination geometry.

Nickel Iron Hydrogenase. The Ni—Fe hydrogenases, when isolated, are found to catalyse both $H_2$ evolution and uptake, with low-potential multihaem cytochromes such as cytochrome $c_3$ acting as either electron donors D or acceptors A, depending on their oxidation state. The Ni—Fe hydrogenases are heterodimeric proteins consisting of small (S) and large (L) subunits. The small subunit contains three iron-sulphur clusters, two $[Fe_4S_4]^{2+/1+}$ and one $[Fe_3S_4]^{1+/0}$; the large subunit contains a nickel-iron centre.

The 3-D structures of the Ni—Fe hydrogenases from *Desulfovibrio gigas* and *Desulfovibrio vulgaris* have been determined. The large subunit is an α/β protein. The active site is dinuclear, containing both Ni and Fe ions placed 2.55-2.9 Å apart. The Ni is pentacoordinated (square pyramidal) with four S atoms of Cys residues being equatorial ligands and the bridging S or O atom an axial ligand. The coordination geometry of the Fe is a slightly distorted octahedron, with three bridging ligands between Ni and Fe (two S of Cys residues and one S or O atom) and three terminal ligands called L1, L2 and L3. In *D. vulgaris* hydrogenase, the larger ligand L1 has been proposed to be S═O, while the smaller ligands L2 and L3 have been assigned as CO or CN⁻. THere is no general agtreement on the catalytic mechanism of Ni—Fe hydrogenase. The small subunit consists of two domains, $I_s$ and $I_s$. The α/β twisted open sheet structure of the N-terminal $I_s$ domain is similar to that of flavodoxin; the C-terminal $II_s$ domain contains two α-helices and no β-structure. The Fe—S clusters are distributed almost along a straight line, with the $[Fe_3S_4]$ cluster located halfway between the two $[Fe_4S_4]$ clusters. The $[Fe_4S_4]_{dist}$ cluster is coordinated by one His and three Cys residues. This is the only known example of histidine acting as a $[Fe_4S_4]$ cluster ligand in protein structure. A crown of acidic residues surrounds the partially exposed His ligand of the $[Fe_4S_4]_{dist}$ cluster and this might provide a recognition site for the redox partner (cytochrome $C_3$).

Hydrogenase accessory proteins. The assembly and insertion of metal clusters into the hydrogenase metalloenzyme requires specific accessory proteins. Such accessory proteins have been identified as members of the Radical SAM (S-adenosylmethionine) superfamily, and have been identified in a number of hydrogenase producing genomes. Radical SAM proteins are frequently involved in the anaerobic synthesis of complex biomolecules and coordinate unusual [FeS] clusters that are often labile.

HydEF encodes a protein with two domains. The N-terminal portion of the HydEF protein is homologous to the radical SAM superfamily, while the C-terminal portion contains a domain with predicted GTPase activity. HydEF and HydG proteins contain a signature Cys-X3-Cys-X2-Cys motif that is typically found within the Radical SAM protein superfamily. This motif coordinates a redox active [4Fe4S] cluster under reducing conditions. The reactions performed by Radical SAM proteins are typically initiated by the generation of a free radical after the reductive cleavage of S-adenosylmethionine at the [4Fe4S] cluster, which yields methionine and a 5'-deoxyadenosyl radical. This high-energy organic radical then abstracts a hydrogen atom from substrates unique to each Radical SAM protein.

HydE, HydF and HydG homologs have been proposed in a number of prokaryotes with iron hydrogenases. In the genomes of *Bacteroides thetaiotaomicron, Desulfovibrio vulgaris, Desulfovibrio desulfuricans*, and *Shewanella oneidensis* the HydE, HydF, and HydG genes form putative operons with [Fe] hydrogenase structural genes, although within the majority of the organisms the accessory proteins are found separated from the structural genes.

Accessory proteins of the invention include enzymes having at least about 20% sequence identity at the amino acid level, more usually at least about 40% sequence identity, and preferably at least about 70% sequence identity to any one of the following above proteins, including Genbank accession AY582739 and AY582740. As with the hydrogenase, the sequences encoding accessory proteins may be codon optimized for the host organism.

Extract source organism. As described above, the coding sequence for one or more hydrogenase accessory proteins are present or introduced into the source organism, and may be present on a replicable vector or inserted into the source organism genome using methods well-known to those of skill in the art. Such vector sequences are well known for a variety of bacteria. The expression vector may further comprise sequences providing for a selectable marker, induction of transcription, etc.

The coding sequences are operably linked to a promoter sequence active in the source organism. Promoters are untranslated sequences located upstream (5') to the start codon of a structural gene (generally within about 100 to 1000 bp) that control the transcription and translation of particular nucleic acid sequence. Promoters may be constitutive or inducible, where inducible promoters initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to accessory protein-encoding DNA by removing the promoter from the source DNA, e.g. by PCR amplification of the sequence, etc. and inserting the isolated sequence into the vector. Both the native hydrogenase promoter sequence and many heterologous promoters may be used for expression, however, heterologous promoters are preferred, such as T7, as they generally permit greater transcription and higher yields. Promoters suitable for use with prokaryotic hosts include the β-lactamase and lactose promoter systems; alkaline phosphatase; a tryptophan (trp) promoter system; an arabinose promoter system; and hybrid promoters such as the tac promoter. However, other known bacterial and bacteriophage promoters are suitable. Their nucleotide sequences have been published, thereby enabling a skilled worker operably to ligate them to DNA encoding hydrogenase accessory proteins.

Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

Host cells are transfected and preferably transformed with the above-described expression or cloning vectors and cultured in conventional nutrient media modified as appropriate for inducing promoters, selecting transformants, and preparing extracts as set forth in the Examples.

Cell-Free Protein Synthesis: as used herein refers to the cell-free synthesis of polypeptides in a reaction mix comprising biological extracts and/or defined reagents. The reaction mix will comprise at least ATP, an energy source; a template for production of the macromolecule, e.g. DNA, mRNA, etc.; amino acids, and such co-factors, enzymes and other reagents that are necessary for the synthesis, e.g. ribosomes, tRNA, polymerases, transcriptional factors, etc. In one embodiment of the invention, the energy source is a homeostatic energy source. Also included may be enzyme(s) that catalyze the regeneration of ATP from high energy phosphate bonds, e.g. acetate kinase, creatine kinase, etc. Such enzymes may be present in the extracts used for translation, or may be added to the reaction mix. Such synthetic reaction systems are well-known in the art, and have been described in the literature. The cell free synthesis reaction may be performed as batch, continuous flow, or semi-continuous flow, as known in the art.

Reaction mix: as used herein refers to a reaction mixture capable of catalyzing the synthesis of polypeptides from a nucleic acid template. The reaction mixture comprises extracts from bacterial cells, e.g. *E. coli* S30 extracts, as described above, and the synthesis is performed under anaerobic conditions. The volume percent of extract in the reaction mix will vary, where the extract is usually at least about 10% of the total volume; more usually at least about 20%; and in some instances may provide for additional benefit when provided at at least about 50%; or at least about 60%; and usually not more than about 75% of the total volume.

REACTION CHEMISTRY

The template for cell-free protein synthesis can be either mRNA or DNA. Translation of stabilized mRNA or combined transcription and translation converts stored information into protein. The combined system, generally utilized in *E. coli* systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally added between 50-250 mM and ammonium between 0-100 mM. The pH of the reaction is generally run between pH 6-9. The temperature of the reaction is generally between about 20° C. and 40° C. These ranges may be extended. It has been found that synthesis of active hydrogenase may benefit from lowered reaction temperatures, where synthesis is performed at a temperature of at least about 20° C., usually at least about 23° C.; and may be about 25° C.; although conventional temperatures for synthesis are not excluded.

The synthesis may be performed for varying lengths of time, depending, in part, on whether the reaction is a batch or continuous feed. For batch reactions, the reactions may continue to accumulate protein for at least about 1 hour, usually at least about 3 hours, more usually at least about 6 hours, and may benefit from reactions time of at least about 12 hours, at least about 18 hours, at least about 24 hours, or longer, particularly where the synthesis is performed at temperatures of less than about 25° C.

The reactions may be large scale, small scale, or may be multiplexed to perform a plurality of simultaneous syntheses. Additional reagents may be introduced to prolong the period of time for active synthesis. Synthesized product is usually accumulated in the reactor, and then is isolated and purified according to the usual methods for protein purification after completion of the system operation. In some cases, enzyme activity may be determined and used without purification.

Of particular interest is the translation of mRNA coupled to in vitro synthesis of mRNA from a DNA template to produce proteins. Such a cell-free system will contain all factors required for the translation of mRNA, for example ribosomes, amino acids, tRNAs, aminoacyl synthetases, elongation factors and initiation factors. Cell-free systems known in the art include *E. coli* extracts, etc., which can be treated with a suitable nuclease to eliminate active endogenous mRNA.

In addition to the above components such as cell-free extract, genetic template, and amino acids, materials specifically required for protein synthesis may be added to the reaction. These materials include salts, polymeric compounds, cyclic AMP, inhibitors for protein or nucleic acid degrading enzymes, inhibitors or regulators of protein synthesis, oxidation/reduction adjusters, non-denaturing surfactants, buffer components, spermine, spermidine, etc.

The salts preferably include potassium, magnesium, ammonium and manganese salts of acetic acid, glutamic acid, or sulfuric acid, and some of these may have other amino acids as a counter anion. The polymeric compounds may be polyethylene glycol, dextran, diethyl aminoethyl dextran, quaternary aminoethyl and aminoethyl dextran, etc. The oxidation/reduction adjuster may be dithiothreitol, ascorbic acid, glutathione and/or their oxides. Also, a non-denaturing surfactant such as Triton X-100 may be used at a concentration of 0-0.5 M. Spermine and spermidine and/or putrescine may be used for improving protein synthetic ability, and cAMP may be used as a gene expression regulator.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

Preferably, the reaction is maintained in the range of pH 5-10 and a temperature of 20°-50° C., and more preferably, in the range of pH 6-9 and a temperature of 20°-35° C., and in the absence of molecular oxygen.

The amount of protein produced in a translation reaction can be measured in various fashions. One method relies on the availability of an assay that measures the activity of the particular protein being translated. Examples of assays for measuring protein activity are the methyl viologen assay described in the examples. These assays measure the amount of functionally active protein produced from the translation reaction. Activity assays will not measure full length protein that is inactive due to improper protein folding or lack of other post translational modifications necessary for protein activity.

An alternative assay for the hydrogenase activity is one that demonstrates actual evolution of $H_2$, as many useful applications of hydrogenase synthesis require the production of hydrogen. To produce hydrogen a reaction must contain a source of electrons, a source of protons, active hydrogenase protein, and an electron carrier that can deliver electrons to hydrogenase. The electron source may be provided as a reduced carrier, e.g. reduced methyl viologen; reduced ferrodoxin; etc. A suitable buffering agent may serve as a source of protons. The candidate synthesis product serves as a source of hydrogenase. Hydrogen is evolved as electrons are donated from the reduced carrier to hydrogenase. Where the carrier provides for a colorimetric change, such as with methyl viologen, the results may be read spectrophotometrically. Alternatively, gas chromatography or other methods may be used to detect the presence of hydrogen evolved from the reaction.

Another method of measuring the amount of protein produced in a combined in vitro transcription and translation reactions is to perform the reactions using a known quantity of radiolabeled amino acid such as $^{35}S$-methionine or $^{14}C$-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications that might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

EXAMPLE 1

Cell Free Synthesis of Active Hydrogenase

The present experiments were done to produce and mature iron hydrogenase using cell free production based on *E. coli* extracts. The bacterial strain used as a source of extract and the extract preparation procedures used for cell-free synthesis were modified to provide appropriate helper proteins. The helper proteins HydG, HydE, and HydF, found in *Shewanella oneidensis* were introduced to aid in the expression of active hydrogenase.

The operon containing the gene that encodes the protein HydG, a small open reading frame named Hydx, and the genes that encode the proteins HydE and HydF from *Shewanella oneidensis* was amplified by PCR and cloned into the commercially available vector pACYC Duet under the control of a single T7 phage promoter. The plasmid containing this operon is hereafter referred to as S.o.HydGxEF. This plasmid was transformed into the commercially available *E. coli* strain BL21(DE3). Transformants were subsequently transformed with another plasmid expressing the HydAI gene from *Chlamydomonas reinhardtii* using the T7 promoter in a pK7-derived plasmid, Kigawa et al. (1995) J. Biomol. NMR 6:129-134. Colonies were screened for hydrogenase activity by anaerobic coexpression of both plasmids in a liquid culture of E. coli. Cells were harvested by centrifugation and resuspended in 2% Triton X-100 buffer to permeabilize cells. A sample of permeabilized cells was added to 2 mM methyl viologen reagent in a quartz cuvette and capped in an atmosphere containing ~5% hydrogen. The development of the blue-colored reduced methyl viologen species indicated the presence of active hydrogenase. Background activity was quantified using a strain expressing β-lactamase from the second plasmid instead of hydrogenase. Having established that coexpression of the proteins on the S.o.HydGxEF plasmid with a heterologous iron hydrogenase gene was sufficient to produce active iron hydrogenase in E. coli, we returned to the strain containing only the S.o.HydGxEF plasmid. This strain, BL21(DE3)+S.o.HydGxEF was then used to make extract for the cell-free production of iron hydrogenases.

Methods for producing active extracts are known in the art, for example they may be found in Pratt (1984), Coupled transcription-translation in prokaryotic cell-free systems, p. 179-209, in Hames, B. D. and Higgins, S. J. (ed.), Transcription and Translation: a practical approach, IRL Press, New York. Kudlicki et al. (1992) *Anal Biochem* 206(2):389-93 modify the S30 E. coli cell-free extract by collecting the ribosome fraction from the S30 by ultracentrifugation. More recently, Liu et al. (2005) *Biotech Prog* 21:460-465 describe a simpler method for extract preparation.

Extract Preparation

E. coli extract preparation for cell-free synthesis has been described by Jewett et al. (2002) in Prokaryotic Systems for in vitro Expression, Eaton Publishing pp 391-411. This method was modified for production of extracts for cell-free synthesis of hydrogenases. The strain BL21(DE3)+S.o-.HydGxEF was grown in defined media. During growth in the 5-liter Bioflow 3000 fermentor (New Brunswick Scientific); temperature, pH, aeration, and agitation were controlled at 37° C., 7.1, 3 SLPM, and 600 rpm, respectively. When the culture reached an optical density (595 nm) of 0.5, IPTG was added to 0.1 mM to induce expression of the T7 RNA polymerase and hence expression of the HydGxEF operon which is transcribed by the T7 RNA polymerase. The culture was incubated under fully aerobic conditions for 1 hour at which time agitation was reduced to 100 rpm and 100% nitrogen was bubbled through the culture at 1 SLPM in place of air. The measured dissolved oxygen in the culture dropped rapidly to zero. Incubation under anaerobic conditions proceeded for 1 hour at which time cells were harvested. Care was taken during the harvest procedure to maintain anaerobiosis by harvesting into a capped flask which was continually flushed with Argon.

Extract was prepared from these E. coli cells similar to published protocols except that all further procedures of extract preparation were executed utilizing an anaerobic chamber which maintains an atmosphere of nitrogen and hydrogen. Any contaminating oxygen is actively scrubbed from the chamber atmosphere by reaction with hydrogen on palladium catalyst. The extract sample was sealed inside the anaerobic chamber before any procedures requiring removal into an aerobic atmosphere such as centrifugation and cell breakage. During the incubation step of extract preparation no reagent or buffer additions were made. Additionally, only one dialysis step of 45 minutes was employed before the extract was aliquotted, sealed in anaerobic vials, and flash frozen using liquid nitrogen. The extract was stored at −80° C. until needed for cell-free protein synthesis. This extract is hereafter referred to as BL21(DE3) Extract #1.

The defined growth medium is as follows:

| Component | g/L |
|---|---|
| $(NH_4)_2SO_4$ | 5 |
| $KH_2PO_4$ | 3 |
| $K_2HPO_4(3H_2O)$ | 6 |
| Na3citrate*2($H_2O$) | 0.8 |
| KCl | 0 |
| Riboflavin (B2) | 0.003647 |
| Thiamine (B1) | 0.016578 |
| Biotin (H) | 0.000108 |
| Cyanoccobalamin (B12) | 8.13E−06 |
| Folic Acid | 6.19E−05 |
| Magnesium Sulfate•$7H_2O$ | 0.23775 |
| Ferric Chloride•$6H_2O$ | 0.01 |
| Sodium Citrate•$2H_2O$ | 0.2 |
| Sodium Molybdate | 0.0035 |
| Sodium Citrate•$2H_2O$ | 0.0375 |
| Boric acid | 0.001213 |
| Cobalt Chloride•$6H_2O$ | 0.003396 |
| Cupric Sulfate•$5H_2O$ | 0.003396 |
| Manganese Sulfate•$H_2O$ | 0.001941 |
| Zinc Sulfate•$7H_2O$ | 0.003396 |
| Sodium Citrate•$2H_2O$ | 0.03 |
| glucose | 9.375 |
| Choline Chloride | 0.026875 |
| Nicotinic Acid (niacin) | 0.023575 |
| PABA | 0.024028 |
| Pantothenic Acid (B5) | 0.008819 |
| Pyridoxine (B6) | 0.001381 |
| Asparagine $H_2O$ | 0.9075 |
| Glycine | 1.3105 |
| Histidine HCl $H_2O$ | 0.2514 |
| Isoleucine | 0.6519 |
| Leucine | 0.6738 |
| Lysine HCl | 0.572 |
| Methionine | 0.2614 |
| Phenylalanine | 0.26175 |
| Proline | 0.87 |
| Threonine | 0.6888 |
| Tryptophan | 0.2648 |
| Tyrosine | 0.3204 |
| Valine | 0.4236 |
| Betaine HCl | 0.6144 |
| Potassium Hydroxide | pH agent |
| Sulfuric Acid | pH agent |

Protocol for Cell-Free Protein Synthesis of Hydrogenase. Freezer stocks of all reagents are put into the anaerobic glove box. They are kept cool with cold blocks and allowed to thaw. For batch reactions, the following reagents are mixed, generally to a final volume of 15 μL:

| | |
|---|---|
| 16 mM Mg(Glutamate)$_2$ | 2.7 mM oxalic acid |
| 10 mM NH$_4$(Glutamate) | 1 mM putrescine |
| 170 mM potassium glutamate | 1.5 mM spermidine |
| 1.2 mM ATP | 5 mM dithiothreitol |
| 0.86 mM GTP | 7 mM cysteine |
| 0.86 mM UTP | 0.15 mM ferrous ammonium sulfate |
| 0.86 mM CTP | 0.1 mM carbamoyl phosphate |
| 34 ug/mL folinic acid | 0.1 mg/mL T7 RNA polymerase |
| 341.2 ug/mL tRNAs | 0.01333 mg/mL plasmid DNA |
| 4 mM twenty amino acids | 0.24 volume fraction anaerobic extract containing HydEFG |
| 0.03 M phosphoenolpyruvate | |
| 0.33 mM NAD | 3 mg/L resazurin (oxygen indicator) |
| 0.27 mM CoA | Water to final volume |

The mixture is incubated at 37° C. or 30° C. for one to three hours. For semi-continuous reactions, the same mixture is placed in a tube with a semi-permeable membrane as its bottom, which is then placed in a bath of three times the reaction volume containing all the above reagents except extract, plasmid, and T7 RNA polymerase. It is incubated anaerobically at 30° C. for one to six hours. A reaction volume of 75 to 200 μL is usually used for semi-continuous reactions.

Results:

CpI is a synthetically constructed, *E. coli* codon-optimized version of the hydrogenase 1 gene from *Clostridium pasteurianum*. sHydA1 is a synthetically constructed, *E. coli* codon-optimized version of the hydrogenase 1 gene from *Chlamydomonas reinhardtii*. CAT is chloramphenicol acetyltransferase, used in this case as a negative control. Activity from this reaction is presumably from *E. coli* hydrogenases in the extract. All three genes were placed in the pK7 plasmid behind a T7 promoter, and were produced by cell-free synthesis as described above.

Figure 2:
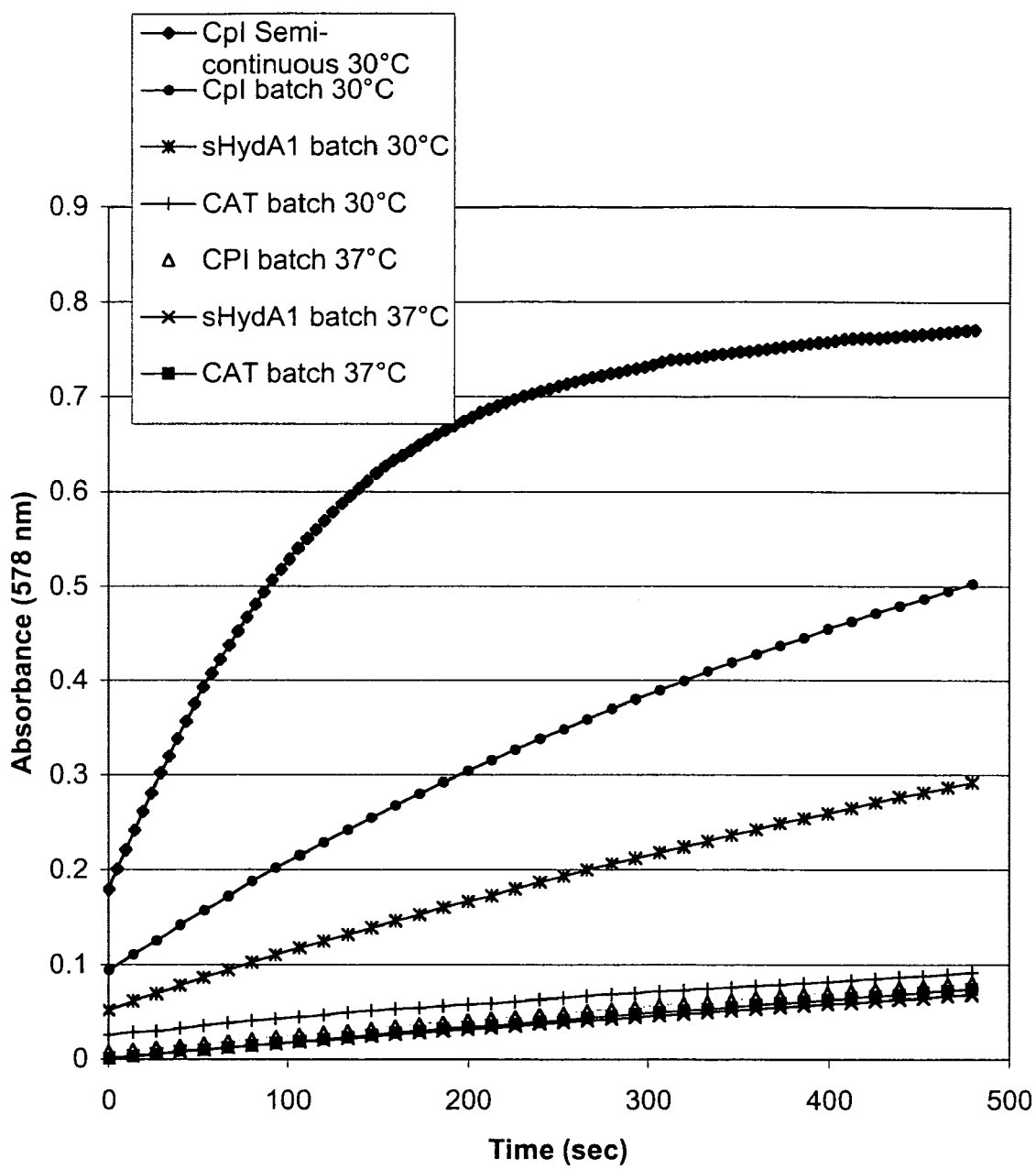
FIG. 2 is a graph depicting hydrogen consumption by hydrogenase produced by cell-free synthesis.

In a standard activity assay, 5 μL of cell-free reaction was added to 700 μL of a solution of 2 mM oxidized methyl viologen in 50 mM Tris at pH 8 and at room temperature. The reduction of methyl viologen by electrons extracted from hydrogen causes the solution to turn blue. The color change was followed spectrophotometrically at a wavelength of 578 nm. The results are shown in FIG. 2. The initial slope of the traces is an indication of the amount of active hydrogenase contained in each assay. A larger slope indicates more hydrogenase activity. A decreasing slope over time indicates that the dissolved hydrogen available to the hydrogenase was being depleted.

No significant difference is shown between the slope produced by the product of the hydrogenase reactions and by the negative control CAT reactions when both were incubated at 37° C. When the reactions were incubated at 30° C., significant activity above background was indicated for reactions producing hydrogenase. Slopes for reaction products produced at 30° C. can be converted to activities using Beer's Law and an extinction coefficient for methyl viologen at 578 nm of 9.78 AU/cm-mM. Two methyl viologen molecules are reduced per hydrogen molecule oxidized. The last column in Table 1 is expressed as hydrogen consumed per mg soluble protein produced in the cell-free reaction. The soluble protein yield of the reactions was determined by measurement of incorporated radioactive leucine, a method known in the art.

TABLE 1

| Hydrogenase | Slope [AU/s] | Slope - Background [AU/s] | d[$H_2$]/dt [mM/s] | Activity [pmol$H_2$/ min-uLrxn] | Activity [μmol$H_2$/ min-mg soluble hydrogenase] |
|---|---|---|---|---|---|
| CpI semicontinuous | 0.0040 | 0.0039 | 0.00020 | 1.67 | 41.6 |
| CpI batch | 0.0012 | 0.0011 | 0.00005 | 0.45 | 11.4 |
| sHydA1 batch | 0.0006 | 0.0005 | 0.00002 | 0.20 | 5.1 |

EXAMPLE 2

Enhanced Production of Hydrogenase at Lower Incubation Temperatures

Cell-free reaction mixtures may be incubated at any temperature desired. Lower temperatures slow protein production rates, but may enhance the ability to properly fold the polypeptide. Data included in Example 1 illustrate an increase of active hydrogenase production at the lower incubation temperature.

Data presented in this example were obtained using a subsequent preparation of cell-free extract from the same strain described in Example 1. In this case, the cells were grown to 0.6 OD before addition of 0.1 mM IPTG to induce helper protein production. At the time of induction sodium fumarate, ferric ammonium citrate, and cysteine were added to final concentrations of 10 mM, 0.1 mg/mL, and 100 μM respectively. The fermentation was then bubbled with 100% nitrogen immediately without further aerobic growth. One hour after induction, the cells were harvested anaerobically as described above. This extract is hereafter referred to as BL21(DE3) Extract #2. Variations in cell breakage efficiency or dilution during dialysis can result in extracts of variable overall concentration. In the case of dilute extracts, it is sometimes useful to increase the overall extract volume fraction in the cell-free reaction mixture beyond that suggested in example 1. Increased amounts of BL21(DE3) Extract #2 were shown to be beneficial for active hydrogenase production.

Figure 3:
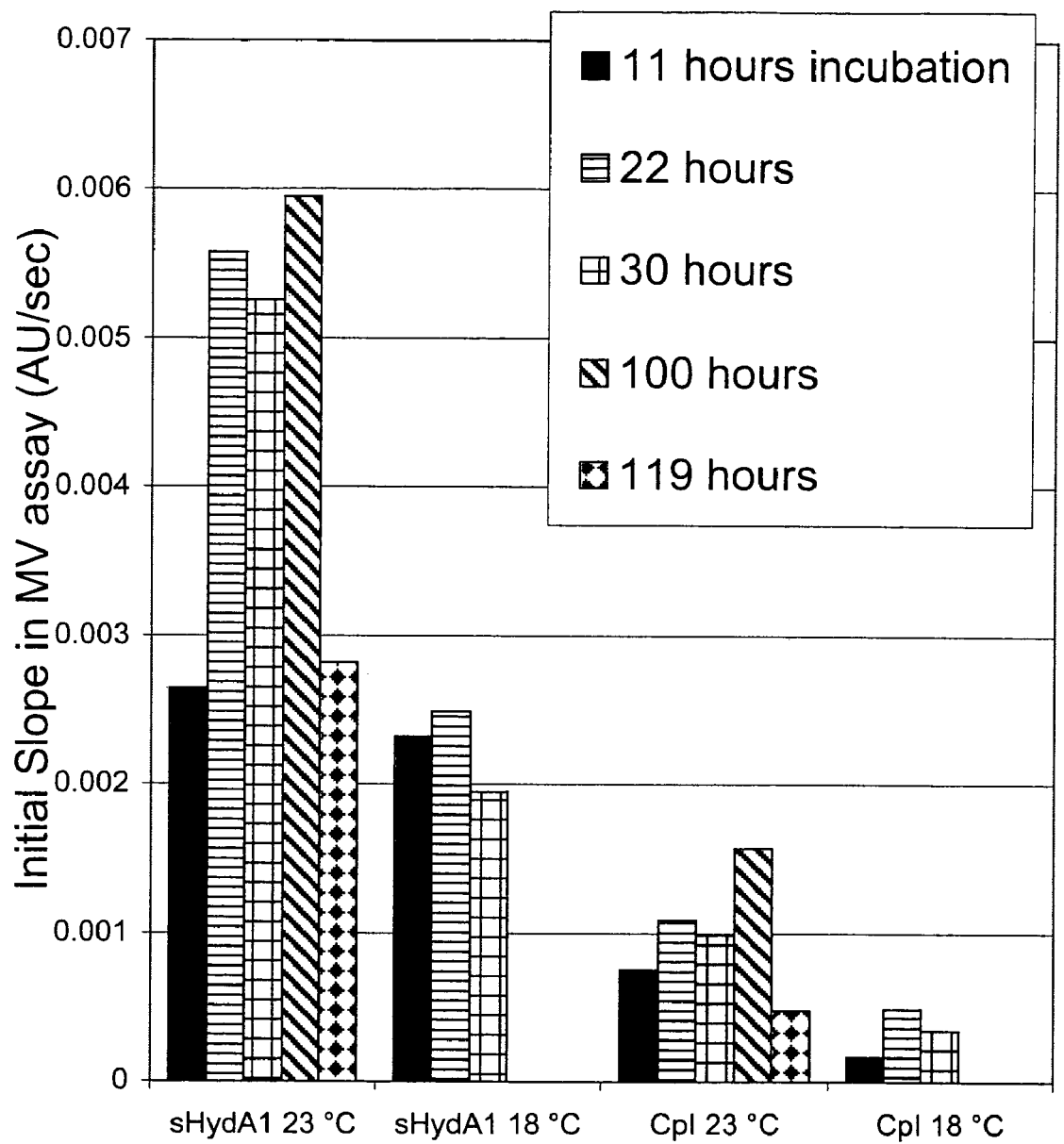
FIG. 3 is a bar graph depicting the activity of hydrogenases produced by the methods of the invention.

To further investigate the effect of temperature, we explored hydrogenase protein expression using incubation at either room temperature (~23° C.), or 18° C. Cell-free reaction mixtures were prepared as described in Example 1 except for using the BL21(DE3) Extract #2 at 0.56 volume fraction. Replicate reactions were prepared so that product accumulation levels and activities could be measured at different times to identify the duration of protein accumulation. FIG. 3 indicates that active hydrogenase accumulates throughout a period of approximately 24 hours. The use of room temperature incubation and longer reaction times results in substantial increases in activity from a batch reaction, especially for the sHydAI hydrogenase. FIG. 3 also illustrates that a further decrease in incubation temperature does not result in increased production of active hydrogenase. Table 2 indicates the maximal activities determined to date for the products of 23° C. cell-free reactions.

TABLE 2

| Hydrogenase | Slope [AU/s] | Slope - Background [AU/s] | d[$H_2$]/dt [mM/s] | Activity [pmol$H_2$/ min-uLrxn] | Activity [μmol$H_2$/ min-mg soluble hydrogenase] |
|---|---|---|---|---|---|
| CpI batch | 0.00157 | 0.00152 | 0.00008 | 0.65 | 14.5 |
| sHydA1 batch | 0.0060 | 0.00059 | 0.00035 | 2.5 | 72.4 |

EXAMPLE 3

Preparation of Active Extract from an Alternate Host Strain

The operon containing HydG, Hydx, HydE, and HydF from *Shewanella oneidensis* was separated by PCR into two fragments, one encoding HydG and Hydx, and the other HydE and HydF. The fragments were cloned behind two arabinose promoters in a newly constructed plasmid named pK7BAD. This plasmid contains the araC gene behind its native promoter and two pBAD promoter regions, each followed by a different restriction endonuclease cloning site and by a transcription terminator. The plasmid is a derivative of the pK7 plasmid described in example 1 in which the T7 promoter region was replaced by the two pBAD expression elements. The hydG+hydx mini-operon was inserted behind the first pBAD promoter, and the hydE+hydF mini-operon was inserted behind the second pBAD promoter to form the pK7BAD So HydGx HydEF plasmid.

The pK7BAD So HydGx HydEF plasmid was transformed into the E. coli strain NMR19. This strain is based on the strain NMR2 which has been previously described. [Michel-Reydellet, and Calhoun. *Metabolic Engineering*. (2004) 6:197-203.] NMR19 also includes deletions in the araBAD and araFGH operons which eliminate arabinose catabolism and the high affinity arabinose transporter. Additionally, the araE gene has been placed behind the Pcp8 promoter in the chromosome to provide constitutive expression of the low-affinity arabinose transporter. These changes were made following a method previously described. [Khlebnikov, et al. *Microbiology-SGM*. (2001) 147: 3241-3247.]

Extract Preparation

The strain BL21(DE3)+S.o.HydGxEF was grown in defined media. During growth, temperature, pH, aeration, and agitation were controlled as described in example 1. When the culture reached an optical density (595 nm) of 2, arabinose was added to 1 mM to induce expression of the HydGxEF genes. Simultaneously, the culture was made anaerobic by bubbling 100% nitrogen through the culture in place of air. Sodium fumarate was added to 10 mM as an electron acceptor to encourage metabolism, and cysteine (5 mM), ferrous ammonium sulfate (0.5 mM), and ferric ammonium citrate (.075 mg/mL) were added to provide sources of sulfur and iron. Incubation under anaerobic conditions proceeded for 1.5 hours at which time cells were harvested. Care was taken during the harvest procedure to maintain anaerobiosis by harvesting into a stoppered flask which was continually flushed with argon. Extract was prepared as described in Example 1. This extract is hereafter referred to as NMR19 Extract #3.

Production of Active Hydrogenase

NMR19 Extract #3 was used to synthesize hydrogenase from the sHydA1 gene using the standard cell-free protein synthesis protocol with a 0.4 volume fraction of extract and a four-hour 30° C. incubation. The standard assay with 2 mM oxidized methyl viologen at pH 8 produced a slope of $3.4 \times 10^{-4}$ AU/s (when 5 µl of the cell-free reaction product was added to 700 µl of the methyl viologen solution), compared to $2.0 \times 10^{-5}$ AU/s for a CAT control. An identical cell-free synthesis reaction, incubated for twenty-four hours at room temperature, gave a slope in the same assay of $6.7 \times 10^{-4}$ AU/s. These activities are lower than those produced in BL21(DE3) extract reactions, but are nonetheless far above CAT and no-DNA background activities. These data indicate the generality of the augmented cell extracts for cell-free hydrogenase production.

EXAMPLE 4

Production of Hydrogen with CFPS-Produced Hydrogenases

Data presented above establish the activity of hydrogenase proteins produced using cell-free synthesis using an assay coupling the consumption of hydrogen with a color change in the compound methyl viologen. Many useful applications of hydrogenase synthesis will require the production of hydrogen. Data presented in this example establish the bidirectionality of the hydrogenase proteins produced using cell-free synthesis by measurement of activity in the hydrogen-producing direction. To produce hydrogen a reaction must contain a source of electrons, a source of protons, active hydrogenase protein, and an electron carrier that can deliver electrons to hydrogenase.

Hydrogen Production as Measured by a Spectrophotometer

Figure 4:
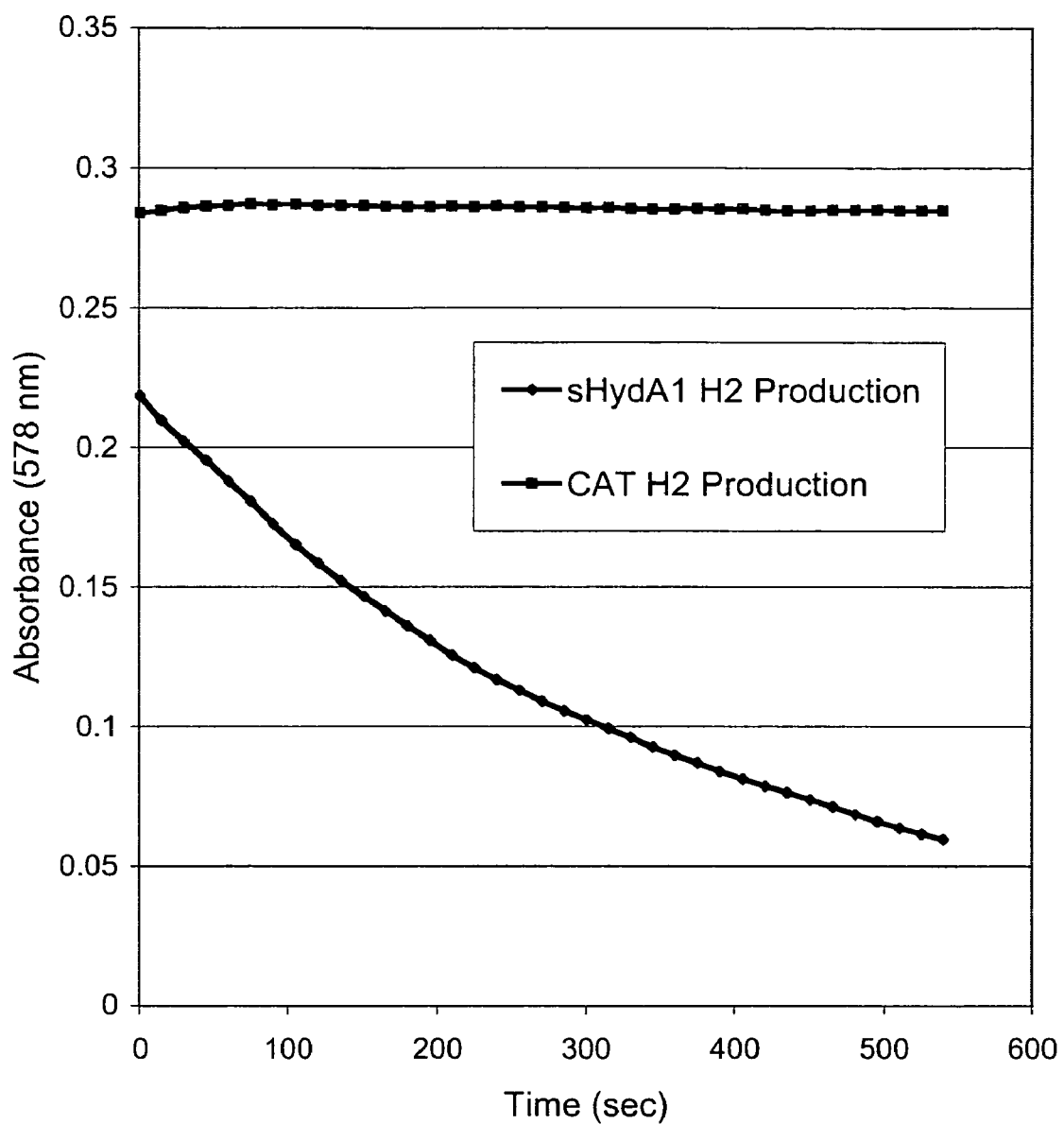
FIG. 4 is a graph depicting the oxidation of methyl viologen by a hydrogenase produced by the methods of the invention

A cell-free reaction mixture was prepared as described in Example 1 using 0.42 volume fraction BL21(DE3) Extract #2 and a DNA template containing the sHydA1 gene, and incubated for 4.5 hours at 30° C. 5 µL of this mixture was combined with 700 µL of 0.1 mM methyl viologen in 2.5 mM Bis-Tris buffer at pH 6.9. The methyl viologen reagent mixture was previously reduced by addition of sodium dithionite until it was dark blue and had a measured absorbance of 0.28. Under these conditions, reduced methyl viologen serves as both an electron source and electron carrier, the buffering agent serves as a source of protons, and the cell-free reaction mixture provides active hydrogenase protein. Hydrogen is evolved as electrons are donated from reduced methyl viologen to hydrogenase. The accompanying oxidation of methyl viologen causes the solution to become clear and the change in solution absorbance is monitored spectrophotometrically at a wavelength of 578 nm. FIG. 4 shows the reduction in solution absorbance for an assay containing HydA1 protein produced by cell-free synthesis. As a negative control, a cell-free synthesis reaction containing the DNA template for CAT was also incubated 24 hours at room temperature. 5 µL of this mixture was added to 700 µL of the reduced methyl viologen solution for comparison. No change in absorbance was observed.

Hydrogen Evolution as Measured by Gas Chromatography

To further illustrate the hydrogen-evolving activity of hydrogenase proteins produced in the cell-free system, we constructed an assay using a gas chromatograph to measure the production of hydrogen. In this assay, a cell-free reaction mixture was prepared as described in Example 1 using BL21(DE3) Extract #1 and DNA template for the CpI protein. This reaction was incubated for 3 hours at 30° C. As a negative control, a similar reaction was prepared using the DNA template for CAT. Following incubation, 30 µL of crude cell-free reaction mixture containing CpI hydrogenase was added to 1 mL of 2 mM methyl viologen solution which was previously reduced by addition of sodium dithionite. Additionally, 100 µL of the cell-free reaction product containing CpI hydrogenase was added to 1 mL of solution containing 50 mM reduced ferredoxin protein from *Synechocystis* sp PCC 6801. The ferredoxin protein was also previously reduced by sodium dithionite. In the above cases, methyl viologen and ferredoxin serve as electron donors to hydrogenase. As a negative control, 150 µL of cell-free reaction product containing the CAT protein was added to 1 mL of solution containing 50 µM reduced ferredoxin.

Figure 5:
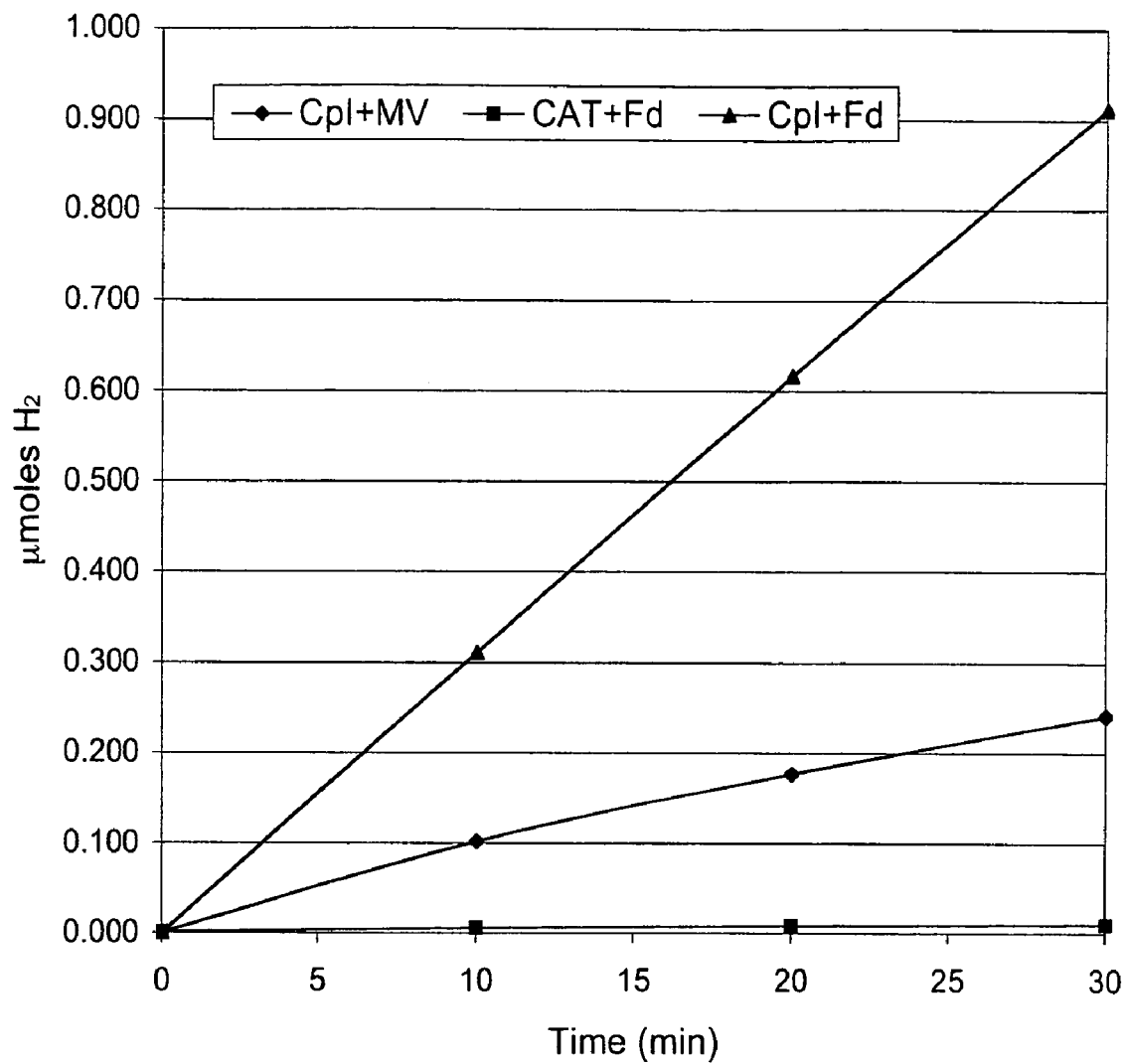
FIG. 5 is a graph depicting hydrogen production with the CpI hydrogenase produced by the methods of the invention and further showing that either reduced methyl viologen or reduced *Synechocystis* ferredoxin can serve as the reductant.

Assay solutions were prepared in stoppered 9 mL vials and the head space of each vial was flushed with oxygen-free argon to purge any hydrogen. The reactions were initiated by injection of the described amount of cell-free reaction product through the stopper using a syringe. 100 µL samples of the head space of the reaction were then removed every ten minutes using a gas-tight syringe and analyzed for hydrogen content using a gas chromatograph. FIG. 5 illustrates the rise in hydrogen content within the vials for assays containing hydrogenase produced by cell-free synthesis. No significant hydrogen accumulation occurs in the vial containing the CAT protein.

Figure 6:
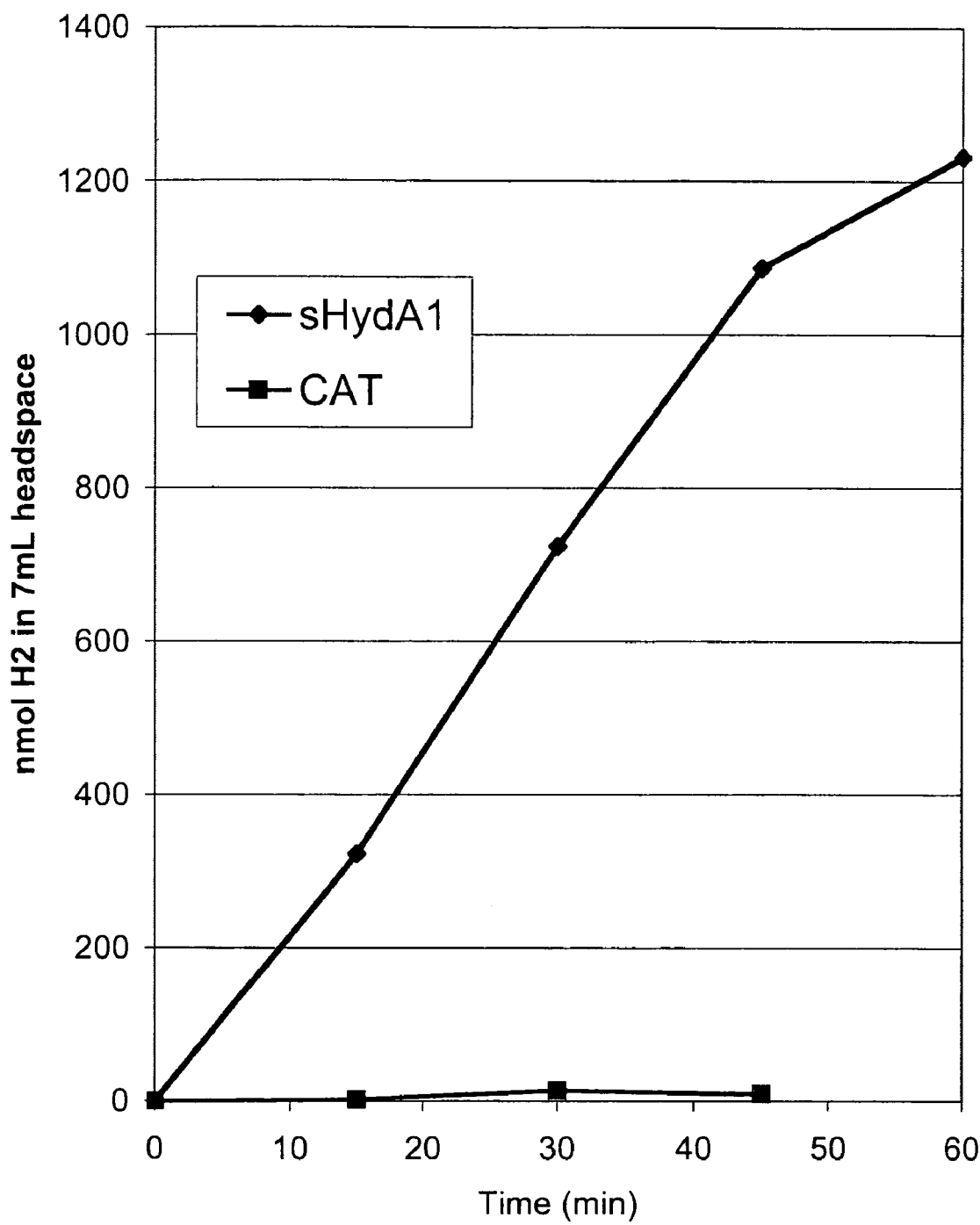
FIG. 6 is a graph depicting hydrogen production with the sHydA1 hydrogenase produced by the methods of the invention.

Hydrogen evolution was also measured directly using cell-free reaction mixtures containing the HydA1 protein. Cell-free reactions were prepared as described in Example 1 using BL21(DE3) Extract #2 and the sHydA1 DNA template. Reactions were incubated for 24 hours at room temperature. An assay solution was prepared by adding 1 mL of a solution containing 5 mM methyl viologen, 25 mM sodium dithionite, and 50 mM Tris-HCl buffer at pH 6.8 into a stoppered vial. The head space of the vial was purged with oxygen-free argon to remove any hydrogen. The reaction was initiated by addition of 10 μL of the cell-free reaction product containing the HydA1 protein, and 100 μL samples of the vial head space were removed into a syringe every 15 minutes. The hydrogen content of the samples was measured using a gas chromatograph. FIG. 6 illustrates the increase in the hydrogen content of the assay vial over time.

The above examples indicate that Fe-only hydrogenases produced using the cell-free system described here are active in both the hydrogen-consuming and hydrogen-producing directions, and that multiple examples of Fe-hydrogenase genes can be produced and activated using multiple cell-free extracts and various production conditions.

It is evident from these results that enzymatically active hydrogenase can be produced in an in vitro, cell-free extract. These data provide a ready source of enzyme for analysis, mutagenesis screening, and the like.

What is claimed is:

1. S30 extract of an *E. Coili* bacterial cell expressing at least one hydrogenase accessory protein encoding gene obtained from *Shewanella oneidensis* wherein said gene is selected from the group consisting of HydE, HydF and HydG genes.

2. The S30 extract of claim 1, wherein said bacterial cell comprises a vector encoding the Shewanella oneidensis HydE, HydF, and HydG genes.

3. The S30 extract of claim 1, wherein said extract is prepared under anaerobic conditions.

4. The 30 extract of claim 1, wherein said extract is provided in a reaction mixture suitable for cell-free polypeptide synthesis.

5. A method of producing enzymatically active hydrogenase protein, the method comprising:
   incubating a polynucleotide encoding a hydrogenase protein of interest in a reaction mixture comprising S30 extract according to any claim 1 under anaerobic conditions for a period of time sufficient to synthesize said polypeptide.

6. The method according to claim 5, wherein said hydrogenase is an iron hydrogenase.

7. The method of claim 6, wherein said iron hydrogenase is a monomeric protein.

8. The method of claim 7, wherein said hydrogenase is selected from the group consisting of *Chlamydomonas reinhardtil* iron-hydrogenase; *Clostridium pasteunanum* hydrogenase; and *Megasphaera elsdenii hydrogenase*.

9. The method of claim 8, wherein said polynucleotide encoding said hydrogenase protein of interest has been codon optimized far said S30 extract source organism.

10. The method of claim 5, wherein said synthesis is performed at a temperature from about 20° C. to about 25° C.

11. The method according to claim 10, wherein said reaction accumulates hydrogenase for at least about 24 hours.

* * * * *

UNITED STATES PATENT AND TRADEMARK OFFICE
CERTIFICATE OF CORRECTION

PATENT NO. : 7,351,563 B2  Page 1 of 1
APPLICATION NO. : 11/149517
DATED : April 1, 2008
INVENTOR(S) : James Robert Swartz It is certified that error appears in the above-identified patent and that said Letters Patent is hereby corrected as shown below:

- Claim 1 col 17 line 21: Insert --A-- at the beginning of the sentence.

- Claim 1 col 17 line 21: Delete "*Coili*" and replace with --*Coli*--.

- Claim 2 col 17 line 26: Delete "Shewanella oneidensis" and replace with --*Shewanella oneidensis*--.

- Claim 5 col 18 line 7: Insert --a-- after the word "comprising".

- Claim 8 col 18 line 16-17: Delete "*reinhardtil*" and replace with --*reinhardtii*--.

- Claim 8 col 18 line 17: Delete "*pasteunanum*" and replace with --*pasteurianum*--.

- Claim 8 col 18 line 18: Delete "*hydrogenase*" and replace with --hydrogenase--.

- Claim 10 col 18 line 24: Delete "20°C. to" and replace with --20°C to--.

Signed and Sealed this

Thirtieth Day of December, 2008

JON W. DUDAS
*Director of the United States Patent and Trademark Office*